US00RE41288E

(19) United States
(12) Reissued Patent
Coolidge et al.

(10) Patent Number: US RE41,288 E
(45) Date of Reissued Patent: Apr. 27, 2010

(54) METABOLIC INTERVENTION WITH GLP-1 OR ITS BIOLOGICALLY ACTIVE ANALOGUES TO IMPROVE THE FUNCTION OF THE ISCHEMIC AND REPERFUSED BRAIN

(75) Inventors: Thomas R. Coolidge, Falls Village, CT (US); Mario R. W. Ehlers, Mercer Island, WA (US)

(73) Assignee: Amylin Pharmaceuticals, Inc., San Diego, CA (US)

(21) Appl. No.: 10/913,309
(22) Filed: Aug. 6, 2004

Related U.S. Patent Documents

Reissue of:
(64) Patent No.: 6,429,197
Issued: Aug. 6, 2002
Appl. No.: 09/303,016
Filed: Apr. 30, 1999

U.S. Applications:
(60) Provisional application No. 60/103,498, filed on Oct. 8, 1998.

(51) Int. Cl.

| | |
|---|---|
| ***A61K 38/26*** | (2006.01) |
| ***A61K 38/28*** | (2006.01) |
| ***A61K 38/16*** | (2006.01) |
| ***A61K 38/00*** | (2006.01) |
| ***C07K 5/00*** | (2006.01) |

(52) U.S. Cl. ..... 514/21; 530/303; 530/308; 530/324; 530/350; 514/2; 514/3; 514/12

(58) Field of Classification Search ..... 514/21, 514/3, 12; 530/303, 308, 324; 424/185.1
See application file for complete search history.

(56) References Cited

U.S. PATENT DOCUMENTS

| | | | | |
|---|---|---|---|---|
| 4,976,959 | A | 12/1990 | Berger, Jr. et al. | |
| 5,373,016 | A | 12/1994 | Brown et al. | |
| 5,424,286 | A * | 6/1995 | Eng | 514/2 |
| 5,574,008 | A | 11/1996 | Johnson et al. | |
| 5,846,937 | A | 12/1998 | Drucker | |
| 6,277,819 | B1 | 8/2001 | Efendic | |
| 6,284,725 | B1 | 9/2001 | Coolidge et al. | |
| 6,894,024 | B2 | 5/2005 | Coolidge et al. | |
| 6,982,248 | B2 | 1/2006 | Coolidge et al. | |

FOREIGN PATENT DOCUMENTS

| | | |
|---|---|---|
| EP | 0708179 A2 | 4/1996 |
| WO | WO 98/08531 | 3/1998 |
| WO | WO 98/30231 | 7/1998 |
| WO | WO 00/16797 A2 | 3/2000 |

OTHER PUBLICATIONS

Green et al. "Animal models of stroke: Do they have value for dsicovering neuroprotive agents?" Trends Pharm. Sci., 2003, 24, 402–8.*

Goke et al. "Exendin–4 is a high potency agonist and truncated exendin–(9–39)–amide an antagonist at the glucagon–like peptide 1–(7–36)–amide receptor of insulin–secreting beta–cells." J. Biol. Chem. 1993, 268, 19650–5.*

Moir, et al. (2006), "Relationship Between Myocardial Perfusion and Dysfunction in Diabetic. . . ", Heart, vol. 92, No. 10, pp. 1414–1419.

Gunn, et al. (1997), "Control of Appetite—The Role of Glucagon–like Peptide–1 (7–36) Amide", J. Endocrinol. vol. 155, No. 2, pp. 197–200.

MacDonald, et al. (2002) Glucagon–like peptide–1 receptor activation anagonizes voltage–dependent repolarizing K(+)currents in beta–cells; a possible glucose–dependent insulinotropic mechanism, Diabetes, vol. 51, Suppl 3, pp. S443–S447.

Doyle, et al. (2001) Insertion of an N–terminal 6–aminohexanoic acid after the 7 amino acid position of glucagon–like peptide–1 produces a long–acting hypoglycemic agent, Endocrinology, vol. 142, No. 10, pp. 4462–4468.

Adler, et al. (2002) UKPDS 59: Hyperglycemia and other potentially modifiable risk factors for peripheral vascular disease in type 2 diabetes, Diabetes Care, vol. 25, No. 5, pp. 894–899.

Boulanger, et al. (2001) Circulating microparticles from patents with myocardial infarction cause endothelial dysfunction, Circulation, vol. 104, No. 22, pp. 2649–2652.

Solh, et al. (2007) Endothelial cell apoptosis in obstructive sleep apnea: a link to endothelial dysfunction, Am. J. Respir. Crit. Care Med., vol. 175, No. 11, pp. 1186–1191.

Warren, et al. (2004) Spinal 2–chloroprocaine: the effect of added dextrose, Anesth Analg., vol. 98, No. 1, pp. 95–101.

Diaz, Rafael, et al, "Metabolic Modulation of Acute Myocardial Infarction the ECLA Glucose–Insulin–Potassium Pilot Trial", Circulation (1998) pp. 2227–2234, 98.

Ryan, Thomas J., et al, "ACC/AHA Guidelines for the Management of Patients with Acute Myocardial Infarction" J. Am. Coll. Cardiol. (1996) pp. 1328–1419.

Voll, C.L., et al, "Postischemic Insulin Reduces Spatial Learning Deficit Following Transient Forebrain in Ischemia Rats", Stroke (1989) pp. 646–651, 20.

Bullock, et al., Endocrinology, (1996) vol. 137, No. 7 pp. 2988–2978.

Hamilton, et al., J. Neurosurg., (Feb. 1995) vol. 82 pp. 262–268.

Irwin, et al., Proc. Natl. Acad. Sci. USA (Jul. 1997) 94, pp. 7915–7920.

Apstein, "Glucose–Insulin–Potassium for Acute Myocardial Infaraction—Remarkable Results from a New Prospective, Randomized Trial", *Circulation*, vol. 98, pp. 2223–2226 (1998).

Partial European Search Report dated Jan. 13, 2005 issued in European Patent Application No. 04027507.5.

* cited by examiner

*Primary Examiner*—Cecilia Tsang
*Assistant Examiner*—Christina Marchetti Bradley

(57) ABSTRACT

It has now been discovered that GLP-1 treatment after acute stroke or hemorrhage, preferably intravenous administration, can be an ideal treatment because it provides a means for optimizing insulin secretion, increasing brain anabolism, enhancing insulin effectiveness by suppressing glucagon, and maintaining euglycemia or mild hypoglycemia with no risk of severe hypoglycemia.

27 Claims, No Drawings

METABOLIC INTERVENTION WITH GLP-1 OR ITS BIOLOGICALLY ACTIVE ANALOGUES TO IMPROVE THE FUNCTION OF THE ISCHEMIC AND REPERFUSED BRAIN

Matter enclosed in heavy brackets [ ] appears in the original patent but forms no part of this reissue specification; matter printed in italics indicates the additions made by reissue.

CROSS REFERENCE TO A RELATED APPLICATION

This application is a continuation-in-part of provisional application No. 60/103,498 filed Oct. 8, 1998.

FIELD OF THE INVENTION

This invention relates to an/effective treatment to improve the function of the ischemic and reperfused brain.

BACKGROUND OF THE INVENTION

Strokes, or cerebrovascular accidents, are the result of an acute obstruction of cerebral blood flow to a region of the brain. There are approximately 500,000 cases each year in the United States, of which 30% are fatal, and hence stroke is the third leading cause of death in the United States. Approximately 80% of strokes are "ischemic" and result from an acute occlusion of a cerebral artery (usually a clot or thrombus), with resultant reduction in blood flow. The remainder are "hemorrhagic", which are due to rupture of a cerebral artery with hemorrhage into brain tissue and consequent obstruction of blood flow due to local tissue compression, creating ischemia.

Stroke commonly affects individuals older than 65 years, and the most powerful risk factor is hypertension. However, there are additional strong risk factors, of which the most important is diabetes mellitus, which confers a two to threefold increased risk and is associated with increased mortality and morbidity after stroke. Moreover, there is strong evidence that hyperglycemia per se, whether associated with diabetes or not, correlates with increased stroke-related mortality and morbidity, although the causal relationship and underlying mechanisms remain controversial.

Until recently, there was no approved therapy for acute stroke, which was treated by general medical support only, followed by rehabilitation from the observed damage. In 1996, the FDA approved the use of tissue plasminogen activator (tPA) as therapy for acute ischemic stroke, based on a limited number of controlled trials. Some, but not all, of the trials revealed a 30–55% improvement in clinical outcome, with an overall reduction in mortality and morbidity. This overall benefit was achieved despite a markedly enhanced risk of intracranial hemorrhage (6.4% of tPA-treated vs. 0.64% in placebo-treated groups), half of which were fatal. Because of concerns about safety and variable efficacy, thrombolytic therapy with tPA has not been universally adopted by clinicians treating acute ischemic stroke. At present, thrombolytic therapy is effectively restricted to major centers with specialized expertise in the management of acute stroke, and it is limited to patients who on CT scanning do not have evidence of major infarction, are less than 70 years old, and are free of major medical conditions including diabetes. As a result, only approximately 1.5% of patients who might be candidates for tPA therapy actually receive it. This situation is likely to improve as clinical experience with its use accumulates and the subset of patients most likely to benefit is more clearly defined. Moreover, there is increasing evidence that spontaneous reperfusion after ischemic stroke improves outcome, which supports the logic of implementing reperfusion therapy.

From these considerations it is evident that there is an enormous unmet need for new, effective therapies for acute stroke. This has stimulated intense research in identifying strategies that can provide neuroprotection during the period of ischemia (whether due to ischemic or hemorrhagic strokes), and therapies that block reperfusion injury following revascularization in ischemic strokes. The goal is to salvage neurons in the so-called ischemic penumbra that surrounds the infarcted core. Candidate agents fall into three major groups: excitotoxicity inhibitors; leukocyte adhesion inhibitors; and neurotrophic factors. In the first group, most efforts are aimed at blocking the action of the excitotoxic neurotransmitter glutamate, mostly by blocking the NMDA class of glutamate receptor. Other strategies include blocking $Na^+$ and $Ca^{2+}$ channels and scavenging nitrous oxide.

The second strategy, blocking leukocyte adhesion, is based on the premise that neutrophils and monocytes contribute significantly to reperfusion injury and infarct zone by administering inhibitors of relevant adhesion molecules and inflammatory cytokines (Jean et al., 1998. Reperfusion injury after focal cerebral ischemia: the role of inflammation and the therapeutic horizon. Neurosurgery 43, 1382–96.)

The third strategy involves the administration of neurotrophic factors that can protect neurons by providing general trophic support during both the ischemic and reperfusion periods. Included in this group of agents are basic fibroblast growth factor and insulin. Numerous studies have shown that insulin can exert potent neuroprotective effects in a variety of stroke models. However, the use of insulin is complicated by the uncertainty surrounding the neurotoxic effects of hyperglycemia, the potential benefits of mild-to-modest hypoglycemia, and the potentially lethal effects of severe hypoglycemia.

In accordance with this invention it can be seen that there is a real and continuing need for an effective treatment to improve the function of the ischemic and reperfused brain. This invention has as its primary object the fulfillment of this need.

Another object of the present invention is to treat the ischemic or reperfused brain with GLP-1 or its biologically active analogues after acute stroke or hemorrhage to optimize insulin secretion, to enhance insulin effectiveness by suppressing glucagon antagonism, and to maintain euglycemia or mild hypoglycemia with no risk of severe hypoglycemia.

Another objective of the present invention is to accomplish the above objectives with a composition that provides no risk of severe hypoglycemia, and can correct hyperglycemia.

A still further objective of the present invention is to provide a treatment with a biologically active compound that offers no side effect risk, whatsoever.

The means and manner of accomplishing each of the above objectives will become apparent from the detailed description of the invention which follows hereinafter.

SUMMARY OF THE INVENTION

It has now been discovered that GLP-1 treatment after acute stroke or hemorrhage, preferably intravenous administration, dan be an ideal treatment because it provides a means for optimizing insulin secretion, increasing brain anabolism, enhancing insulin effectiveness by suppressing glucagon, and maintaining euglycemia or mild hypoglycemia with no risk of severe hypoglycemia or other adverse side effects.

DETAILED DESCRIPTION OF THE INVENTION

Numerous animal and human studies have revealed a strong correlation between hyperglycemia and the severity of stroke-related morbidity and mortality. However, there is considerable disagreement about whether high blood glucose levels actually contribute to neuronal injury during ischemia, or whether hyperglycemia is merely a secondary stress response to neuronal injury. A recent retrospective follow-up study of 811 patients with acute stroke in the U.K. concluded that hyperglycemia predicts higher mortality and morbidity independently of other adverse prognostic factors and thus may be casually related to neuronal damage. However, this conclusion has been challenged by some on statistical grounds, and there is a consensus in some quarters that hyperglycemia in stroke patients is reactive to cerebral damage rather than causative. Nevertheless, it is remarkable that 20% to 43% of acute stroke patients are hyperglycemic at presentation. This can be accounted for, in part, by preexisting diabetes (25% to 50% of hyperglycemic patients), but in the majority this appears to be a reflection of an acute stress response with an increased production of cortisol, glucagon, and catecholamines. Whether the resulting hyperglycemia is in fact causally related to neuronal injury in human stroke patients cannot be answered definitively at present.

Attempts to clarify the role of hyperglycemia in producing neuronal damage have focused on appropriate animal models of acute stroke. These studies have revealed that in rat models of transient focal cerebral ischemia followed by reperfusion—a model relevant to the clinical situation of ischemic stroke treated by tPA revascularization—hyperglycemia appears to be causally related to enhanced neuronal damage. Compared to focal ischemia, models of global ischemia, induced either by transient cardiac arrest or by bilateral vessel occlusion in rats, revealed a less significant neurotoxic effect of hyperglycemia. Experiments in these global ischemia models have revealed that insulin-induced normo- or hypoglycemia are neuroprotective, but that these effects appear to be mediated by insulin directly, independent of its blood glucose-lowering action. Thus, experiments in animals indicate that the neuronal effects of blood glucose during and after acute stroke are complex, and depend both on the extent of the ischemic zone and on the timing of blood glucose manipulations.

The consequences of ischemia-reperfusion events, whether focal or global, are reversible and irreversible brain cell damage, cell death, and decreased organ functional efficiency.

The paradox of cellular damage associated with a limited period of ischemic anoxia followed by reperfusion is that cell damage and death appear not only likely to directly result from the period of oxygen deprivation but, additionally, as a consequence of re-oxygenation of tissues rendered highly sensitive to oxidative damage during the ischemic period. Reperfusion damage begins with the initial oxidative burst immediately upon reflow and continues to worsen over a number of hours an inflammatory processes develop in the same post-ischemic tissues. Efforts dedicated to decreasing sensitivity of post-anoxic cells to oxidative damage and, additionally, efforts to reduce inflammatory responses in these same tissues have been shown to reduce the reversible and irreversible damage to post-anoxic reperfused organs. A combination of methods to reduce both the initial oxidative burst injury and subsequent inflammation associated damage could provide synergistic protection against reperfusion injury. GLP-1, and its biologically-active analogues, can accomplish this by creating a strong anabolic effect on brain cells.

In addition to GLP-1 or its biological analogues, the therapy can include use of free radical scavengers such as glutachione, melatonin, Vitamin E and [superoxide dismuture (]SOD[)]. In this combination, reperfusion damage risk is even lessened further.

With respect to the treatment of such patients, a common therapy now used is to employ thrombolytics such as streptokinase and t-PA. U.S. Pat. No. 4,976,959 discloses the administration of t-PA and SOD to inhibit tissue damage during reperfusion. Thus, an increasing number of patients are being exposed to the likelihood of reperfusion injury and its effects resulting from thrombolytic interventions.

The inventors here have discovered that the administration of human GLP-1, or its biologically active analogues, enhanced or restored insulin secretion responses with the insulin being neuroprotective, likely by direct neurotrophic effects, as well as by controlling stroke-related hyperglycemia.

The term "GLP-1", or glucagon-like peptide, includes GLP-1 mimetics and its biologically active analogues as used in the context of the present invention, and can be comprised of glucagon-like peptides and related peptides and analogs of glucagon-like peptide-1 that bind to a glucagon-like peptide-1 (GLP-1) receptor protein such as the GLP-1 (7–36) amide receptor protein and has a corresponding biologically effect on insulin secretion as GLP-1 (7–36) amide, which is a native, biologically active form of GLP-1. See Goke, B. and Byrne, M, Diabetic Medicine. 1996, 13:854–860. The GLP-1 receptors are cell-surface proteins found, for example, on insulin-producing pancreatic β-cells. Glucagon-like peptides and analogues will include species having insulinotropic activity and that are agonists of, i.e. activate, the GLP-1 receptor molecule and its second messenger activity on, inter alia, insulin producing β-cells. Agonists of glucagon-like peptide that exhibit activity through this receptor have been described: EP 0708179A2; Hjorth, S. A. et al., J. Biol. Chem. 269 (48):30121–30124 (1994); Siegel, E. G. et al. Amer. Diabetes Assoc. 57th Scientific Sessions, Boston (1997); Hareter, A. et al. Amer. Diabetes Assoc. 57th Scientific Sessions, Boston (1997); Adelhorst, K. et al. J. Biol. Chem. 269(9):6275–6278 (1994); Deacon C. F. et al. 16th International Diabetes Federation Congress Abstracts, Diabetologia Supplement (1997); Irwin, D. M. et al., Proc. Natl. Acad. Sci. USA. 94:7915–7920 (1997); Mosjov, S. Int. J. Peptide Protein Res. 40:333–343 (1992). Glucagon-like molecules include polynucleotides that express agonists of GLP-1, i.e. activators of the GLP-1 receptor molecule and its secondary messenger activity found on, inter alia, insulin-producing β-cells. GLP-1 mimetics that also are agonists of β-cells include, for example, chemical compounds specifically designed to active the GLP-1 receptor. Recent publications disclose Black Widow GLP-1 and $Ser^2$ GLP-1, see G. G. Holz, J. F. Hakner/Comparative Biochemistry and Physiology, Part B 121(1998)177–184 and Ritzel, et al., A Synthetic glucagon-like peptide-1 analog with improved plasma stability, J. Endocrinol 1998 October;159(1):93–102. Glucagon-like peptide-1 antagonists are also known, for example see e.g. Watanabe, Y. et al., J. Endocrinol. 140(1):45–52 (1994), and include exendin (9–39) amine, an exendin analog, which is a potent antagonist of GLP-1 receptors (see, e.g. WO97/46584).

Further embodiments include chemically synthesized glucagon-like polypeptides as well as any polypeptides or fragments thereof which are substantially homologous. "Substantially homologous," which can refer both to nucleic acid and amino acid sequences, means that a particular subject sequence, for example, a mutant sequence, varies from a reference sequence by one or more substitutions, deletions, or additions, the net effect of which does not result in an adverse functional dissimilarity between reference and subject sequences. For purposes of the present invention, sequences having greater than 50 percent homology, and preferably greater than 90 percent homology, equivalent biological activity in enhancing β-cell responses to plasma glucose levels, and equivalent expression characteristics are considered substantially homologous. For purposes of determining homology, truncation of the mature sequence should be disregarded. Sequences having lesser degrees of homology, comparable bioactivity, and equivalent expression characteristics are considered equivalents.

Mammalian GLP peptides and glucagon are encoded by the same gene. In the ileum the phenotype is processed into two major classes of GLP peptide hormones, namely GLP-1 and GLP-2. There are four GLP-1 related peptides known which are processed from the phenotypic peptides. GLP-1 (1–37) has the sequence His Asp Glu Phe Glu Arg His Ala Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ ID NO:1). GLP-1 (1–37) is amidated by post-translational processing to yield GLP-1 (1–36) $NH_2$ which has the sequence His Asp Glu Phe Glu Arg His Ala Glu Gly Thr Phe Thr Ser Asp Val Ser Ser Tyr Leu Glu Gly Gln Ala Ala Lys Glu Phe Ile Ala Trp Leu Val Lys Gly Arg ($NH_2$) (SEQ ID NO:2); or is enzymatically processed to yield GLP-1 (7–37) which has the sequence His Ala Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ ID NO:3). GLP-1 (7–37) can also be amidated to yield GLP-1 (7–36) amide which is the natural form of the GLP-1 molecule, and which has the sequence His Ala Glu Gly Thr Phe Thr Ser Asp Val Ser.

Ser Tyr Leu Glu Gly Gln Ala Ala Lys Glu Phe Ile Ala Trp Leu Val Lys Gly Arg ($NH_2$)(SEQ ID NO:4) and in the natural form of the GLP-1 molecule.

Intestinal L cells secrete GLP-1 (7–37)(SEQ ID NO:3) and GLP-1(7–36)$NH_2$ (SEQ *ID* NO:4) in a ratio of 1 to 5, respectively. These truncated forms of GLP-1 have short half-lives in situ, i.e., less than 10 minutes, and are inactivated by an aminodipeptidase IV to yield Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ ID NO:5) and Glu Gly Thr Phe Thr Ser Asp Val Ser Ser Tyr Leu Glu Gly Gln Ala Ala Lys Glu Phe Ile Ala Trp Leu Val Lys Gly Arg ($NH_2$)(SEQ ID NO:6), respectively. The peptides Glu Gly Thr Phe Thr Ser Asp Val Ser Ser Tyr Leu Glu Gly Gln Ala Ala Lys Glu Phe Ile Ala [Tip] *Trp* Leu Val Lys Gly Arg Gly (SEQ ID NO:5) and Glu Gly Thr Phe Thr Ser Asp Val Ser Ser Tyr Leu Glu Gly Gln Ala Ala Lys Glu Phe Ile Ala Trp Leu Val Lys Gly Arg ($NH_2$)(SEQ ID NO:6), have been speculated to affect hepatic glucose production, but do not stimulate the production or release of insulin from the pancreas.

There are six peptides in Gila monster venoms that are homologous to GLP-1. Their sequences are compared to the sequence of GLP-1 in Table 1.

TABLE 1

| | | |
|---|---|---|
| a. | H A E G T F T S D V S S Y L E G Q A A K E F I A W L V K G R $NH_2$ | *(SEQ ID NO: 4)* |
| b. | H S D G T F T S D L S K Q M E E E A V R L F I E W L K N G G P S S G A P P P S $NH_2$ | *(SEQ ID NO: 7)* |
| c. | D L S K Q M E E E A V R L F I E W L K N G G P S S G A P P P S $NH_2$ | *(SEQ ID NO: 8)* |
| d. | H G E G T F T S D L S K Q M E E E A V R L F I E W L K N G G P S S G A P P P S $NH_2$ | *(SEQ ID NO: 9)* |
| e. | H S D A T F T A E Y S K L L A K L A L Q K Y L E S I L G S S T S P R P P S S $NH_2$ | *(SEQ ID NO: 10)* |
| f. | H S D A T F T A E Y S K L L A K L A L Q K Y L E S I L G S S T S P R P P S $NH_2$ | *(SEQ ID NO: 11)* |
| g. | H S D A I F T E E Y S K L L A K L A L Q K Y L A S I L G S R T S P P P $NH_2$ | *(SEQ ID NO: 12)* |
| h. | H S D A I F T Q Q Y S K L L A K L A L Q KY L A S I L G S R T S P P P $NH_2$ | *(SEQ ID NO: 13)* |

The major homologies as indicated by the outlined areas in Table 1 are: peptides c and h are derived from b and g, respectively. All 6 naturally occurring peptides (a, b, d, e, f and g) are homologous in positions 1, 7, 11 and 18. GLP-1 and exendins 3 and 4 (a, b and d) are further homologous in positions 4, 5, 6, 8, 9, 15, 22, 23, 25, 26 and 29. In position 2, A, S and G are structurally similar. In position 3, residues D and E (Asp and Glu) are structurally similar. In positions 22 and 23 F (Phe) and I (Ile) are structurally similar to Y (Tyr) and L (Leu.), respectively. Likewise, in position 26 L and I are structurally equivalent.

Thus, of the 30 residues of GLP-1, exendins 3 and 4 are identical in 15 positions and equivalent in 5 additional positions. The only positions where radical structural changes are evident are at residues 16, 17, 19, 21, 24, 27, 28 and 30. Exendins also have 9 extra residues at the carboxyl terminus.

The GLP-1 like peptides can be made by solid state chemical peptide synthesis. GLP-1 can also be made by conventional recombinant techniques using standard procedures described in, for example, Sambrook and Maniaitis. "Recombinant", as used herein, means that a protein is derived from recombinant (e.g., microbial or mammalian) expression systems which have been genetically modified to contain an expression gene for GLP-1 or its biologically active analogues.

The GLP-1 like peptides can be recovered and purified from recombinant cell cultures by methods including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. High performance liquid chromatography (HPLC) can be employed for final purification steps.

The polypeptides of the present invention may be a naturally purified product, or a product of chemical synthetic procedures, or produced by recombinant techniques from prokaryotic or eukaryotic hosts (for example by bacteria, yeast, higher plant, insect and mammalian cells in culture or in vivo). Depending on the host employed in a recombinant production procedure, the polypeptides of the present invention are generally non-glycosylated, but may be glycosylated.

GLP-1 activity can be determined by standard methods, in general, by receptor-binding activity screening procedures which involve providing appropriate cells that express the GLP-1 receptor on their surface, for example, insulinoma cell lines such as RINmSF cells or INS-1 cells. See also Mosjov, S. (1992) and EP0708170A2. In addition to measuring specific binding of tracer to membrane using radioimmunoassay methods, cAMP activity or glucose dependent insulin production can also be measured. In one method, a polynucleotide encoding the receptor of the present invention is employed to transfect cells to thereby express the GLP-1 receptor protein. Thus, for example, these methods may be employed for screening for a receptor agonist by contacting such cells with compounds to be screened and determining whether such compounds generate a signal, i.e. activate the receptor.

Polyclonal and monoclonal antibodies can be utilized to detect purify and identify GLP-1 like peptides for use in the methods described herein. Antibodies such as ABGA1178 detect intact unspliced GLP-1 (1–37) or N-terminally-truncated GLP-1 (7–37) or (7–36) amide. Other antibodies detect on the very end of the C-terminus of the precursor molecule, a procedure which allows by subtraction to calculate the amount of biologically active truncated peptide, i.e. GLP-1 (7–37) or (7–36) amide. (Orskov et al. Diabetes, 1993, 42:658–661; Orskov et al. J. Clin. Invest. 1991, 87:415–423).

Other screening techniques include the use of cells which express the GLP-1 receptor, for example, transfected CHO cells, in a system which measures extracellular pH or ionic changes caused by receptor activation. For example, potential agonists may be contacted with a cell which expresses the GLP-1 protein receptor and a second messenger response, e.g. signal transduction or ionic or pH changes, may be measured to determine whether the potential agonist is effective.

The glucagon-like peptide-1 receptor binding proteins of the present invention may be used in combination with a suitable pharmaceutical carrier. Such compositions comprise a therapeutically effective amount of the polypeptide, and a pharmaceutically acceptable carrier or excipient. Such a carrier includes, but is not limited, to saline, buffered saline, dextrose, water, glycerol, ethanol, lactose, phosphate, mannitol, arginine, trehalose and combinations thereof. The formulations should suit the mode of administration and are readily ascertained by those of skill in the art. The GLP-1 peptide may also be used in combination with agents known in the art that enhance the half-life in vivo of the peptide in order to enhance or prolong the biological activity of the peptide. For example, a molecule or chemical moiety may be covalently linked to the composition of the present invention before administration thereof. Alternatively, the enhancing agent may be administered concurrently with the composition. Still further, the agent may comprises a molecule that is known to inhibit the enzymatic degradation of GLP-1 like peptides may be administered concurrently with or after administration of the GLP-1 peptide composition. Such a molecule may be administered, for example, orally or by injection.

The dose range of concentrations that are effective depend somewhat upon the manner of administration, i.e., sustained release or continuous, such as intravenous infusion or subcutaneous infusion. However, since GLP-1 has no side effects, considerable leeway can be tolerated. It can be given in a bolus administration, either I.V. or subcutaneous as well.

Although not limited to the following ranges and provided only as an illustration, suggested dose ranges for various applications are for continuous infusion by intravenous (I.V.) 0.1 pmol/kg/min to 10 pmol/kg/min and by subcutaneous (s.c.) 0.1 pmol/kg/min to 75 pmol/kg/min, and for single injection (bolus) by I.V. 0.1 nmol/kg to 2.0 nmol/kg and s.c. 0.1 nmol/kg to 100 nmol/kg.

The preferred method of administration of the GLP-1 peptide is through a continuous application at a dosing rate within a range of from about 1 to about 10 pmol/kg per minute of GLP-1 delivered by sustained release subcutaneous, intramuscular, interperitoneal, injected depot with sustained release, deep lung insufflation, as well as by intravenous, buccal, patch or other sustained release delivery methods.

The possible mechanisms of glucose neurotoxicity remain speculative, and Applicants do not wish to be bound by a theory. However, during cerebral ischemia, as in other tissues, anaerobic glycolysis is stimulated and produces lactic acid, which is likely enhanced by hyperglycemia. Lactate may be especially toxic to ischemic neuronal cells. A second possibility is that hyperglycemia causes increased leakage of red blood cells through the ischemic capillary endothelium, producing micro-hemorrhagic infarcts. A third mechanism that has been suggested is that neuronal excitotoxicity (e.g., induced by glutamate) is glucose-sensitive and hence hyperglycemia enhances this potent source of neuronal damage. Despite not knowing the precise mechanism, the fact is treatment with GLP-1 provides significant benefits.

Importantly, and as a preventive of heightened damage and risk, GLP-1 can be and should be administered as soon as it is sensed that an event has, or is occurring. Thus it can be administered at home or in an ambulance for its immediate anabolic effect to improve brain metabolism.

From these considerations it is clear that a potentially important strategy in treating acute stroke and in limiting infarct size is controlling hyperglycemia, reducing blood glucose levels to the normo- or modest hypoglycemia range. And, until now, the only practical means of treating hyperglycemia was with insulin.

To date, no randomized, controlled human trial has been completed to examine the benefits of insulin treatment for acute stroke, although such trials have been advocated. However, the insulin side effect risk is too great. In contrast to this paucity of data in human trials, numerous studies have evaluated the effects of insulin in animal models of stroke. Virtually without exception, these studies have documented strong benefits, indicating that insulin preserves functional capacity, limits infarct size, land reduces mortality after both global ischemia and focal ischemia with reperfusion. In models of global ischemia, in which both carotid arteries were occluded, in some cases with induced hypotension, or in which asphyxial cardiac arrest was induced, insulin had a remarkable protective effect, limiting infarct size, reducing the neurological deficit, and enhancing the metabolic recovery. Moreover, the effect of insulin was largely independent of its blood glucose-lowering action; indeed, profound hypoglycemia was uniformly detrimental to cerebral function and outcome.

In models of transient focal cerebral ischemia, insulin similarly had a strong protective effect, reducing infarct volume and extent of cerebral necrosis, (Yip, P K, He, Y Y, Hsu, C Y, Garg, N, Marangos, P, and Hogan, E L (1991) Effect of plasma glucose on infarct size in focal cerebral ischemia-reperfusion. Neurology 41, 899–905; Hamilton, M G, Tranmer, B I, and Auer, R N (1995) Insulin reduction of cerebral infarction due to transient focal ischemia. J. Neurosurg. 82, 262–268).

The powerful neuroprotective effect of insulin has been examined mechanistically by White and colleagues (White, B C, Grossman, L I, and Krause, G S (1993) Brain injury by global ischemia and reperfusion: A theoretical perspective on membrane damage and repair. Neurology 43, 1656–1665; White, B C, Grossman, L I, O'Neil, B J, DeGracia, D J, Neumar, R W, Rafols, J A, and Krause, G S (1996) Global brain ischemia and reperfusion. Ann. Emerg. Med. 27, 588–594). These authors have argued that insulin acts as a potent neurotrophic factor that can activate general neuronal repair pathways that are independent of its effects on glucose metabolism. During stroke most of the structural damage occurs during reperfusion. This is thought to arise from ischemia-induced membrane lipolysis, local accumulation of membrane fatty acids, and subsequent superoxide production during reperfusion-stimulated oxidation of these fatty acids. The reperfusion-generated oxygen radicals then damage neuronal membranes by lipid peroxidation. This injury is aggravated by reperfusion-induced suppression of protein synthesis, which disables membrane repair systems. In this setting, insulin and other members of the insulin-like growth factor (IGF) family have major neuron-salvaging effects by stimulating protein synthesis and up-regulating the machinery for new membrane lipid synthesis: This, in turn, may stem from insulin-stimulated dephosphorylation of eukaryotic initiation factor-2 (elF-2$\alpha$), thereby promoting effective translation of mRNA transcripts.

EXAMPLES

In accordance with this invention the use of GLP-1 (glucagon-like peptide-1 [7–36] amide) is an ideal alternative to insulin for the treatment of acute stroke. This is because of the glucose-dependent insulinotropic action of GLP-1. Endogenous insulin secretion is stimulated by GLP-1 in the presence of normo- to hyperglycemia, but not during hypoglycemia, thus protecting against the development of severe hypoglycemia. This means that in a type II diabetic, GLP-1 will stimulate a sustained secretion of insulin and will tend to normalize blood glucose levels. Both of these actions can be of enormous benefit in the acute stroke situation. Similar results can be achieved in non-diabetic stroke patients with reactive hyperglycemia. In stroke victims with euglycemia, GLP-1 will result in a modest insulin secretion, which may return to baseline in the absence of supplemental glucose. In such cases, it may be desirable to coadminister intravenous glucose (low-dose, e.g. 5%) in order to maintain stimulation of insulin secretion. Unlike a glucose-insulin infusion, however, there will be no need for careful dose titration, since the glucose-dependent action of GLP-1 results in "auto-titration" with maintenance of euglycemia coupled with elevated circulating insulin levels.

Circulating FFAs are not now thought to enter the brain and are not a fuel source for the brain. When fully oxygenated, the brain metabolizes glucose exclusively, and only switches to liver-derived ketone bodies during prolonged starvation. During ischemia, aerobic glucose oxidation is impaired and glycolysis is enhanced, but this fails to generate sufficient ATP. As a result, membrane functions are impaired, $Ca^{2+}$ enters cells, and enzymatic lipolysis of neuronal membrane phospholipids is stimulated, generating intracerebral FFAs. These FFAs are not generated by the action of glucagon. Nevertheless, suppression of glucagon may generally enhance the metabolic milieu, by reducing the stress-induced state of insulin antagonism. With enhanced metabolic milieu there should be a beneficial suppression of inflammation.

It can be seen from the above examples which are illustrative only of one aspect of the present invention that it accomplishes all of its stated objectives. Importantly, these examples should be in no way taken as a limitation of the teachings or the disclosure or the range or equivalence of the present invention, as they are exemplary only.

SEQUENCE LISTING

```
<160> NUMBER OF SEQ ID NOS: 13

<210> SEQ ID NO 1
<211> LENGTH: 37
<212> TYPE: PRT
<213> ORGANISM: Homo sapiens

<400> SEQUENCE: 1

His Asp Glu Phe Glu Arg His Ala Glu Gly Thr Phe Thr Ser Asp Val
  1               5                  10                  15

Ser Ser Tyr Leu Glu Gly Gln Ala Ala Lys Glu Phe Ile Ala Trp Leu
             20                  25                  30

Val Lys Gly Arg Gly
         35


<210> SEQ ID NO 2
<211> LENGTH: 36
```

-continued

<212> TYPE: PRT
<213> ORGANISM: Homo sapiens

<400> SEQUENCE: 2

His Asp Glu Phe Glu Arg His Ala Glu Gly Thr Phe Thr Ser Asp Val
1 5 10 15

Ser Ser Tyr Leu Glu Gly Gln Ala Ala Lys Glu Phe Ile Ala Trp Leu
20 25 30

Val Lys Gly Arg
35

<210> SEQ ID NO 3
<211> LENGTH: 31
<212> TYPE: PRT
<213> ORGANISM: Homo sapiens

<400> SEQUENCE: 3

His Ala Glu Gly Thr Phe Thr Ser Asp Val Ser Ser Tyr Leu Glu Gly
1 5 10 15

Gln Ala Ala Lys Glu Phe Ile Ala Trp Leu Val Lys Gly Arg Gly
20 25 30

<210> SEQ ID NO 4
<211> LENGTH: 30
<212> TYPE: PRT
<213> ORGANISM: Homo sapiens

<400> SEQUENCE: 4

His Ala Glu Gly Thr Phe Thr Ser Asp Val Ser Ser Tyr Leu Glu Gly
1 5 10 15

Gln Ala Ala Lys Glu Phe Ile Ala Trp Leu Val Lys Gly Arg
20 25 30

<210> SEQ ID NO 5
<211> LENGTH: 29
<212> TYPE: PRT
<213> ORGANISM: Homo sapiens

<400> SEQUENCE: 5

Glu Gly Thr Phe Thr Ser Asp Val Ser Ser Tyr Leu Glu Gly Gln Ala
1 5 10 15

Ala Lys Glu Phe Ile Ala Trp Leu Val Lys Gly Arg Gly
20 25

<210> SEQ ID NO 6
<211> LENGTH: 28
<212> TYPE: PRT
<213> ORGANISM: Homo sapiens

<400> SEQUENCE: 6

Glu Gly Thr Phe Thr Ser Asp Val Ser Ser Tyr Leu Glu Gly Gln Ala
1 5 10 15

Ala Lys Glu Phe Ile Ala Trp Leu Val Lys Gly Arg
20 25

<210> SEQ ID NO 7
<211> LENGTH: 39
<212> TYPE: PRT
<213> ORGANISM: Heloderma suspectum

<400> SEQUENCE: 7

His Ser Asp Gly Thr Phe Thr Ser Asp Leu Ser Lys Gln Met Glu Glu

-continued

```
  1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35


<210> SEQ ID NO 8
<211> LENGTH: 31
<212> TYPE: PRT
<213> ORGANISM: Heloderma suspectum

<400> SEQUENCE: 8

Asp Leu Ser Lys Gln Met Glu Glu Glu Ala Val Arg Leu Phe Ile Glu
  1               5                  10                  15

Trp Leu Lys Asn Gly Gly Pro Ser Ser Gly Ala Pro Pro Pro Ser
            20                  25                  30


<210> SEQ ID NO 9
<211> LENGTH: 39
<212> TYPE: PRT
<213> ORGANISM: Heloderma suspectum

<400> SEQUENCE: 9

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35


<210> SEQ ID NO 10
<211> LENGTH: 38
<212> TYPE: PRT
<213> ORGANISM: Heloderma suspectum

<400> SEQUENCE: 10

His Ser Asp Ala Thr Phe Thr Ala Glu Tyr Ser Lys Leu Leu Ala Lys
  1               5                  10                  15

Leu Ala Leu Gln Lys Tyr Leu Glu Ser Ile Leu Gly Ser Ser Thr Ser
            20                  25                  30

Pro Arg Pro Pro Ser Ser
        35


<210> SEQ ID NO 11
<211> LENGTH: 37
<212> TYPE: PRT
<213> ORGANISM: Heloderma suspectum

<400> SEQUENCE: 11

His Ser Asp Ala Thr Phe Thr Ala Glu Tyr Ser Lys Leu Leu Ala Lys
  1               5                  10                  15

Leu Ala Leu Gln Lys Tyr Leu Glu Ser Ile Leu Gly Ser Ser Thr Ser
            20                  25                  30

Pro Arg Pro Pro Ser
        35


<210> SEQ ID NO 12
<211> LENGTH: 35
<212> TYPE: PRT
<213> ORGANISM: Heloderma suspectum
```

-continued

```
<400> SEQUENCE: 12

His Ser Asp Ala Ile Phe Thr Glu Glu Tyr Ser Lys Leu Leu Ala Lys
  1               5                  10                  15

Leu Ala Leu Gln Lys Tyr Leu Ala Ser Ile Leu Gly Ser Arg Thr Ser
             20                  25                  30

Pro Pro Pro
         35


<210> SEQ ID NO 13
<211> LENGTH: 35
<212> TYPE: PRT
<213> ORGANISM: Heloderma suspectum

<400> SEQUENCE: 13

His Ser Asp Ala Ile Phe Thr Gln Gln Tyr Ser Lys Leu Leu Ala Lys
  1               5                  10                  15

Leu Ala Leu Gln Lys Tyr Leu Ala Ser Ile Leu Gly Ser Arg Thr Ser
             20                  25                  30

Pro Pro Pro
         35
```

What is claimed is:

1. A method of [increasing insulinotropic response in ischemia] *treating reperfusion*-injured brain cells *after an ischemic event* comprising administering a composition containing glucagon-like peptide-1 (GLP-1) and a pharmaceutical carrier for a time sufficient and under conditions effective to [increase insulinotropic response which produces insulin, with the produced insulin being neuroprotective by direct neurotropic effects and by controlling stroke-related hyperglycemia] *treat reperfusion injury*.

2. The method of claim 1 wherein the pharmaceutical carrier is selected from the group consisting of saline, buffered saline, dextrose, water, glycerol, ethanol, lactose, phosphate, mannitol, arginine, treholose, and [combinations] *mixtures* thereof.

3. The method of claim 1 wherein the administration commences within 4 hours of an ischemic event.

4. The method of claim 1 wherein the administration of the composition is continuous and intravenously at 0.1 pmol/kg/min to 10 pmol/kg/min.

5. The method of claim 1 wherein the administration of the composition is a bolus subcutaneous injection at 0.1 nmol/kg to 75 nmol/kg.

6. The method of claim 1 wherein the administration is by a method selected from the group consisting of *intravenous, intramuscular, intraperitoneal,* subcutaneous or micropressure injection, deep lung insufflation, external or implant pump, depot injection, [and other sustained release mechanisms,] buccal, [and other cross skin and membrane mechanisms] *and patch sustained release delivery mechanisms*.

[7. The method of claim 1 wherein the composition is administered intravenously at a dose of 0.1 pmol/kg/min up to 10 pmol/kg/min.]

8. The method of claim [7] *1* further comprising concurrent administration of glucose.

9. The method of claim [7] *1* further comprising concurrent administration of an oxygen scavenger.

[10. A method of increasing insulinotropic response in ischemia injured brain cells comprising administering to an individual in need of such treatment a dose of 0.1 pmol/kg/min to 10 pmol/kg/min of a composition containing glucagon-like peptide-1 (GLP-1) and a pharmaceutical carrier for a time sufficient and under conditions effective to increase insulinotropic response which produces insulin, with the produced insulin being neuroprotective by direct neurotropic effects and by controlling stroke-related hyperglycemia.]

*11. The method of claim 1 further comprising administering a thrombolytic agent.*

*12. A method of treating or ameliorating injury to brain cells in a subject following reperfusion after a period of ischemia comprising administering a composition comprising a glucagon-like peptide-1 (GLP-1) mimetic and a pharmaceutical carrier for a time sufficient and under conditions effective to treat or ameliorate said injury.*

*13. The method of claim 12 wherein said GLP-1 mimetic is GLP-1(1–37), GLP-1(1–36) amide, GLP-1(7–37), GLP-1 (7–36) amide or mixtures thereof.*

*14. The method of claim 12 wherein said GLP-1 mimetic is an exendin.*

*15. The method of claim 14 wherein said exendin is exendin-3.*

*16. The method of claim 14 wherein said exendin is exendin-4.*

*17. The method of claim 12 wherein said subject is not hyperglycemic.*

*18. A method of treating or ameliorating reperfusion injury to brain cells following stroke in a subject in need thereof, comprising administering a composition comprising an exendin to said subject for a time sufficient and under conditions effective to treat or ameliorate the reperfusion injury.*

*19. The method of claim 18 wherein said exendin is exendin-3.*

*20. The method of claim 18 wherein said exendin is exendin-4.*

*21. The method of claim 18 wherein said subject is not hyperglycemic.*

*22. The method of claim 18 wherein said stroke is ischemic.*

*23. The method of claim 18 wherein said stroke is hemorrhagic.*

*24. The method of claim 18 further comprising administering a thrombolytic agent.*

*25. The method of claim 18 wherein the administration is by a method selected from the group consisting of intravenous, intramuscular, interperitoneal, subcutaneous or micropressure injection, deep lung insufflation, depot injection, buccal, patch, and sustained release delivery methods.*

*26. A method of treating or ameliorating injury to brain cells in a subject following a period of ischemia comprising administering a composition comprising an exendin and a pharmaceutical carrier.*

*27. The method of claim 27 wherein said exendin is exendin-4.*

*28. The method of claim 27 further comprising administering a thrombolytic agent.*

*29. The method of claim 27 wherein the injury is caused by reperfusion.*

* * * * *